/

US005734168A

United States Patent [19]
Yao

[11] Patent Number: 5,734,168
[45] Date of Patent: Mar. 31, 1998

[54] MONOLITHIC STRUCTURE WITH INTERNAL COOLING FOR MEDICAL LINAC

[75] Inventor: Chong-Guo Yao, Pachaco, Calif.

[73] Assignee: Siemens Medical Systems, Inc., Iselin, N.J.

[21] Appl. No.: 668,583

[22] Filed: Jun. 20, 1996

[51] Int. Cl.$^6$ .................................................. H05H 9/00
[52] U.S. Cl. ........................................ 250/492.3; 315/5.41
[58] Field of Search ........................... 250/492.3, 492.1; 315/5.41, 5.51, 500, 505; 313/359.1, 360.1

[56] References Cited

U.S. PATENT DOCUMENTS

| | | | |
|---|---|---|---|
| 3,449,618 | 6/1969 | Gallagher | 315/5.41 |
| 3,453,483 | 7/1969 | Leidigh | 315/5.51 |
| 4,324,980 | 4/1982 | Symmons | 250/505.1 |
| 4,350,921 | 9/1982 | Liska et al. | 315/5.41 |
| 4,988,919 | 1/1991 | Tanabe et al. | 315/5.41 |
| 5,021,741 | 6/1991 | Kornely, Jr. et al. | 328/227 |
| 5,381,072 | 1/1995 | Tanabe | 315/5.41 |
| 5,538,494 | 7/1996 | Matsuda | 250/492.3 |

OTHER PUBLICATIONS

Schonberg, R.G., et al., "Portable, X-Band, Linear Accelerator Systems," Schonberg Radiation Corporation, Mountain View, California. have no date and pages.

Primary Examiner—Michael J. Tokar
Assistant Examiner—Kiet T. Nguyen

[57] ABSTRACT

In a clinical linear accelerator system for delivering charged particles for medical applications, a series of monolithic cavity-defining members is connected to form a succession of accelerating cavities, with temperature regulation being achieved by aligning internal cooling passageways through the series of monolithic members. As a result, a continuous coolant flow path is formed through the monolithic members. At each member-to-member interface, there is a leakage-release path for non-intrusively conducting any leakage that occurs at the interface. In the preferred embodiment, there is a braze connection that separates the leakage-release path at an interface from the coolant flow path at that interface. The braze connection provides a seal that further safeguards against coolant entering an area in which performance of the system is affected.

14 Claims, 3 Drawing Sheets

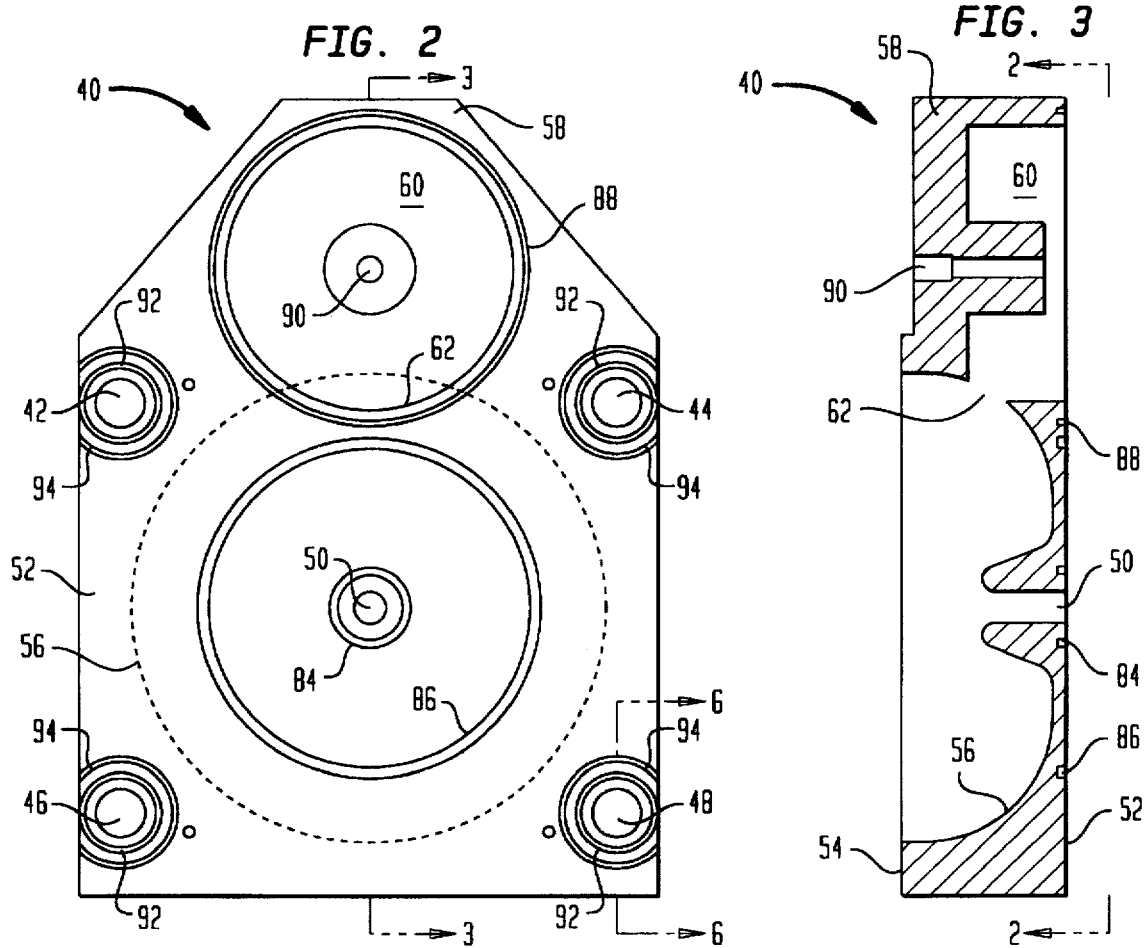
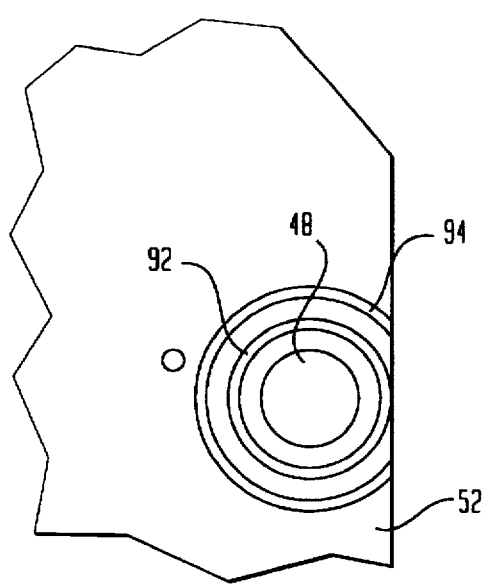
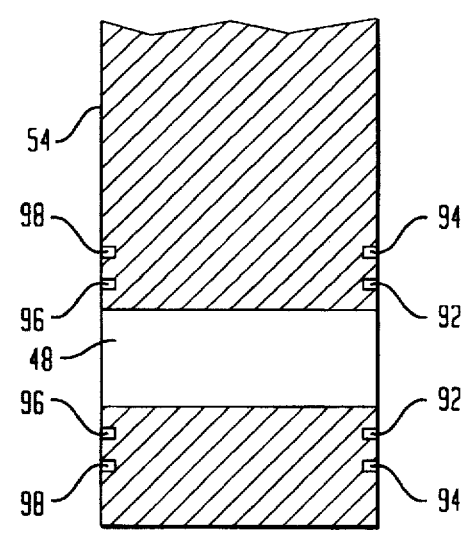

MONOLITHIC STRUCTURE WITH INTERNAL COOLING FOR MEDICAL LINAC

BACKGROUND OF THE INVENTION

The invention relates generally to clinical devices for radiation therapy and more particularly to temperature regulation of a linear accelerator that is utilized for medical purposes.

DESCRIPTION OF THE RELATED ART

Linear accelerators may be used in a medical environment for a variety of applications. A beam of charged particles, e.g. electrons, from a linear accelerator may be directed at a target which is made of a material having a high atomic number, so that an X-ray beam is produced for radiation therapy. Alternatively, the beam of charged particles may be applied directly to a patient during a radiosurgical procedure. Such radiosurgery has become a well-established therapy in the treatment of brain tumors. A high-energy beam may be directed at a localized region to cause a breakdown of one or both strands of the DNA molecule inside cancer cells, with the goal of at least retarding further growth and preferably providing curative cancer treatment.

U.S. Pat. No. 4,324,980 to Symmons describes a conventional linear accelerator ("linac") for use in medical radiotherapy. The linac includes a series of accelerating cavities that are aligned along a beam axis. A particle source, which is typically an electron gun, directs charged particles into the first accelerating cavity. As the charged particles travel through the succession of accelerating cavities, the particles are focused and accelerated by means of an electromagnetic field. For example, a radio frequency (RF) source may be coupled to the accelerator to generate the necessary field to operate the linac. The accelerated particles from a clinical linac have a high energy, e.g. 4 MeV. Often, the output beam is directed to a magnetic bending system that functions as an energy filter. The beam is bent by approximately 270°. Then either the output beam of high energy particles or an X-ray beam generated by impinging a target with the output beam is employed for radiation treatment of a patient.

The frequency of the driving signal source and the dimensions of the accelerating cavities and the beam passages between adjacent accelerating cavities determine the operating frequency of the clinical accelerator. Optimal performance of the accelerator requires a match between the resonant frequency of the cavity structure and the frequency of the driving signal.

It is important that the beam characteristics of the output from the clinical accelerator remain constant during specific therapy treatments. Moreover, the beam characteristics should be consistent among successive treatments. One difficulty in maintaining this consistency is that the acceleration operation results in the generation of thermal energy. The cavity structure of clinical accelerators is conventionally a number of cell or half-cell members that are brazed together. The cell members are formed of copper, which is a material having a relatively high coefficient of thermal expansion. The thermal expansion results in thermal detuning of the cavity structure. The driving signal may be adjusted to compensate for some thermal detuning, but performance will be affected.

The Symmons patent illustrates the conventional approach of controlling thermal expansion of the cell members. The cell members are brazed together and are then connected to a conduit. A coolant, such as deionized water, is conducted through the conduit. Thermal energy is conducted from the cell members to the coolant, thereby providing a degree of thermal regulation. In addition to the external cooling, an electron exit window is internally cooled by milling a C-shaped groove into a base plate that is covered by a cover plate. When a coolant is conducted through the groove, heat is dissipated from a target to the coolant.

While Symmons teaches internal cooling at the electron exit window assembly of a clinical accelerator, the patent follows the conventional approach of utilizing external cooling for the assembly of cell members that define the accelerating cavities of a clinical linac. Linear accelerators that have been manufactured for applications outside of the medical environment utilize more extensive internal cooling. A white paper entitled "Portable, X-band, Linear Accelerator Systems," by R. G. Schoenberg et al. describes an electron accelerator used for applications such as X-ray inspection of nuclear power plant piping welds. An X-ray head is described as having internal water cooling passages. The self-contained cooling water supply provides temperature controlled water for the accelerator section in the X-ray head and the magnetron, the RF circulator, and the high power RF load in the RF head.

Another form of internal cooling for a linear accelerator adapted for applications outside of the medical environment is described in U.S. Pat. No. 5,021,741 to Kornely, Jr. et al. Each drift tube in a series of drift tubes is separately cooled. For each drift tube, coolant-circulating grooves are integrally formed in the central body of the drift tube, as well as in the opposed face plates. The face plates are attached to the central body of the particular drift tube by solder/ electroform techniques. Coolant both enters and exits the drift tube through a stem having concentric passages. The patent asserts that by providing a cast drift tube, the likelihood of coolant leakage is reduced relative to drift tubes that are formed by manufacturing and machining a number of components which are then brazed together. The reduced number of interfaces within the Kornely, Jr. et al. drift tube results in a reduction of the number of potential areas of coolant leakage. Isolating the coolant flows through the different drift tubes is described as being consistent with the prior art, and is consistent in minimizing the number of interfaces through which coolant must flow.

What is needed is a clinical linear accelerator having enhanced thermal regulation relative to conventional accelerators adapted for medical purposes, without increasing the susceptibility of the clinical device to leakage-related problems.

SUMMARY OF THE INVENTION

In a clinical device for linearly accelerating charged particles along a beam axis for medical purposes, an assembly comprises a series of interconnected monolithic cavity-defining members that form successive accelerating cavities aligned along the beam axis. Internal cooling is provided by interconnecting coolant passages to form at least one continuous coolant flow path through the monolithic members. In one embodiment, at the interfaces between abutting monolithic members, leak-release paths are formed about the coolant passages, so that any leakage is not intrusive.

BRIEF DESCRIPTION OF THE DRAWINGS

FIG. 2 is a front view of a monolithic cavity-defining member having coolant passageways for providing the internal cooling capability of the clinical linear accelerator of FIG. 1.

FIG. 3 is a side sectional view of the monolithic member of FIG. 2, taken along lines 2—2.

FIG. 5 is an expanded view of one of the coolant passageways of FIG. 2.

FIG. 6 is a side sectional view of the coolant passageway of FIG. 2, taken along lines 6—6.

DETAILED DESCRIPTION

Figure 1:
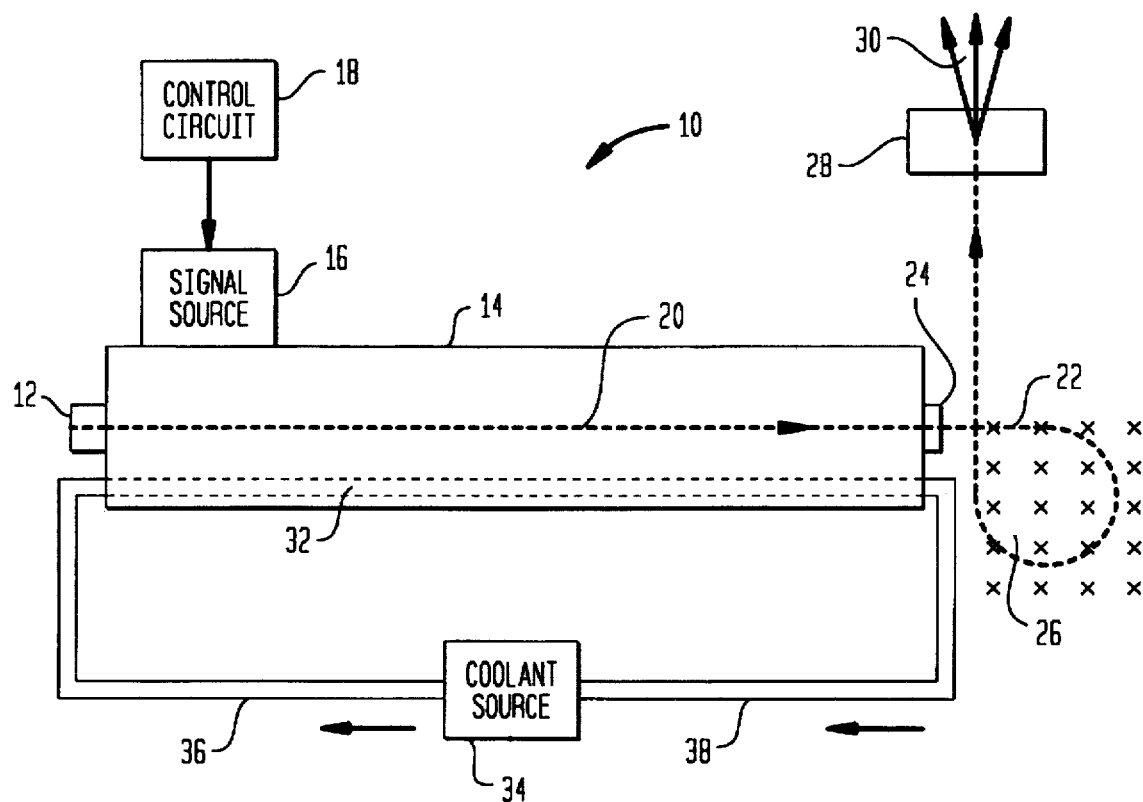
FIG. 1 is a schematical view of a clinical linear accelerator having internal cooling in accordance with the invention.

With reference to FIG. 1, a clinical linear accelerator system 10 for medical treatment is shown as having a particle source 12 for directing charged particles into an accelerator device 14, which is also referred to as a waveguide. In the preferred embodiment, the particle source is an electron gun which injects electrons into the input end of the accelerator device. The electron gun is a conventional component of clinical linear accelerators ("linacs").

A driving signal is introduced into the accelerator device 14 by a signal source 16. The signal source introduces an electromagnetic wave having a suitable frequency. Radio frequency or high frequency sources are conventionally employed, but the selection of the frequency of the drive signal is not critical to the invention. Optionally, the frequency is dynamically controlled by a control circuit 18 that is connected within a closed loop system, not shown.

Electrons introduced into the accelerator device 14 by the electron gun 12 are accelerated along the beam axis 20 of the device. The electrons obtain a high energy by virtue of the energy-transfer relationship with the electromagnetic waves established by connection with the signal source 16. A pulsed or steady-state output beam 22 of electrons is emitted from an exit window 24, which is located at the delivery end of the device 14. While it is not critical to the invention, the exit window conventionally includes a thin metal foil.

The output beam 22 of charged particles is directed to a magnetic bending system 26, which acts as an energy filter. The output beam is bent by approximately 270°, and is then directed onto a target 28, such as a gold or tungsten target. Impingement of the target by the output beam 22 generates an X-ray beam 30 which is employed for radiation treatment of a patient. Alternatively, the output beam 22 can be applied directly to a patient such as during a radiosurgical procedure to treat a brain tumor. The operations of the magnetic bending system 26 and the target 28 are well known by persons skilled in the art.

Conventionally, thermal regulation of the accelerator device is achieved by attaching an external conduit along the exterior surface of the device. For example, copper pipe may be placed in contact with the exterior of the device, with a coolant, such as deionized water, passing through the pipe to conduct thermal energy away from the device.

In contrast to the conventional approach, the linac system 10 of FIG. 1 utilizes internal cooling. That is, there is an internal coolant flow path 32 through the accelerator device 14. By utilizing the internal coolant flow path that will be described in greater detail below, a significantly enhanced thermal coupling between the liquid coolant and the structure to be thermally regulated is achieved. One concern in providing an internal path for liquid flow is that accelerator devices for clinical linacs are typically formed by brazing a series of cell members or half-cell members, so that there are a number of member-to-member interfaces that are encountered as the liquid flows from an input end to the output end of the flow path. Each interface is a potential area of coolant leakage, which can enter the accelerating cavities of the device. However, the interfaces of adjacent monolithic half-cell members to be described below include leakage-release paths to safeguard against the detrimental effects of coolant leakage.

The cooling system includes a source 34 of coolant into a device-input conduit 36 and receives a return flow from a device-output conduit 38.

While the accelerator device 14 is shown as having a single internal coolant flow path 32, there are preferably a number of flow paths. The input and output conduits 36 and 38 may be connected to each of the flow paths, or there may be a separate conduit for each flow path. In the preferred embodiment, there are four parallel internal coolant flow paths. As another alternative to the embodiment of FIG. 1, the coolant flow path through the accelerator device 14 is non-linear. A non-linear flow path may offer some advantages with regard to conducting thermal energy from the device. Nevertheless, the linear flow path of FIG. 1 is preferred, since it provides advantages with regard to ease of manufacture.

Referring now to FIGS. 2 and 3, a monolithic half-cell member 40 is shown as having four internal coolant passageways 42, 44, 46 and 48. Each of the four coolant passageways is a portion of a different coolant flow path 32 described with reference to FIG. 1. The four coolant passageways are symmetrically arranged about a beam-axis opening 50. The opening 50 extends from a first face 52 of the monolithic member to the interior of the monolithic member. A second face is contoured to provide an abutment region 54 and a cavity-defining region 56. As best seen in FIG. 2, the cavity-defining region 56 has a circular cross section. An exemplary maximum diameter of the cavity-defining region is 7.64 cm. This maximum is reached at the inner edges of the abutment region 54.

Figure 4:
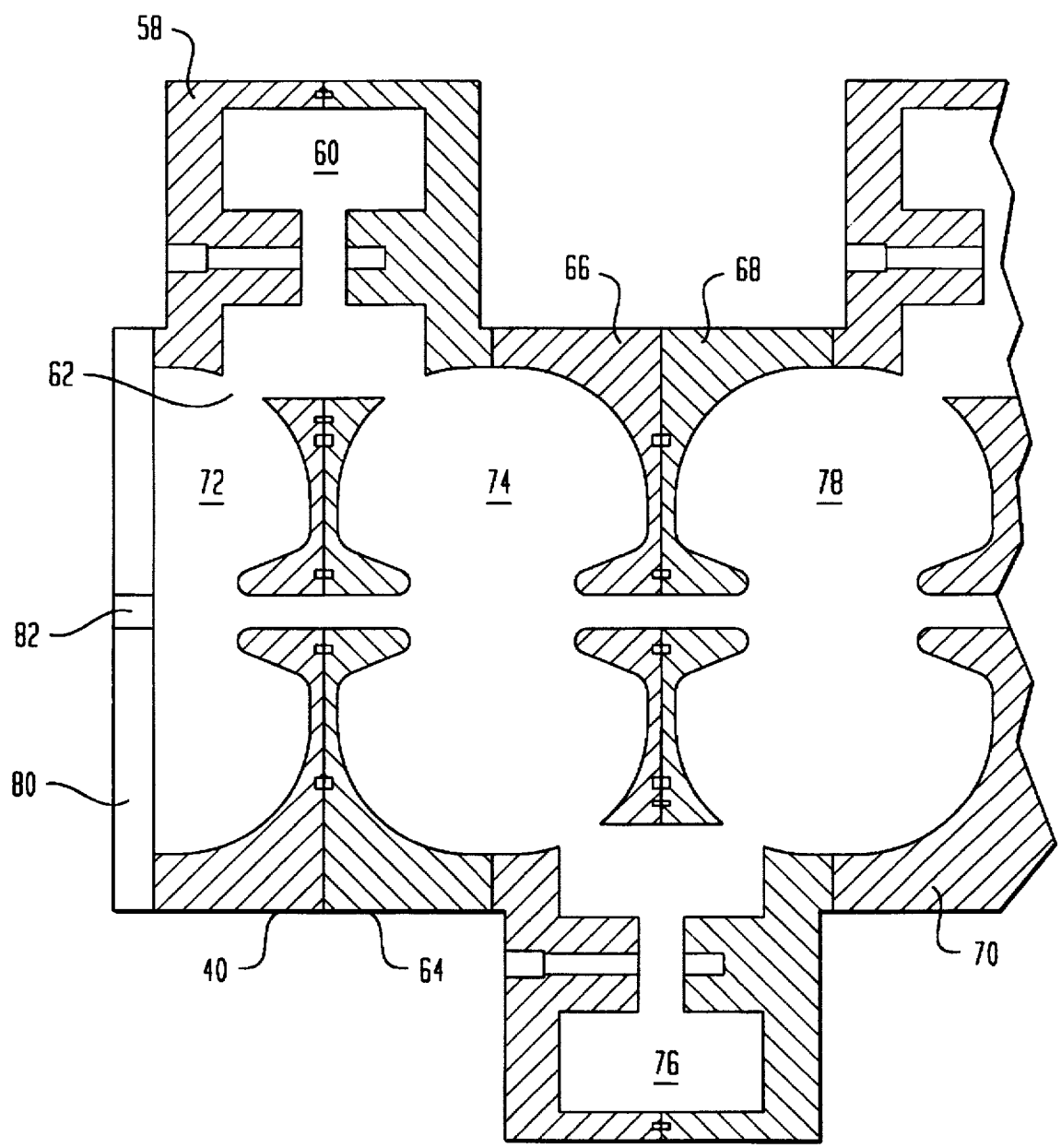
FIG. 4 is a side sectional view of a series of monolithic members that are connected to form an accelerator device.

The half-cell member 40 is a monolithic side-coupled structure. The side coupling is achieved by means of the upper portion 58 of the monolithic member. This upper portion is machined to provide a coupling cavity 60. The coupling cavity is off-axis of the electron beam and is connected to the accelerating cavity of the monolithic member by an opening 62. FIG. 4 shows five monolithic half-cell members 40, 64, 66, 68 and 70 connected together to form a portion of an accelerating device. The upper portion of the half-cell member 64 which is brazed to the first surface of the half-cell member 40 completes the coupling cavity 60. The coupling cavity 60 is connected to each of two accelerating cavities 72 and 74. A second coupling cavity 76 is opened to the accelerating cavity 74 and a third accelerating cavity 78. Consequently, when a drive signal having the appropriate frequency is fed to the coupling cavities, the electromagnetic waves are in an energy-transfer relationship with an electron beam that is directed through the accelerating cavities. The accelerating device of FIG. 4 operates in the standing wave mode that is also referred to as a "half-pi mode." Known standing-wave accelerator coupling cavities may also take the form of on-axis, coaxial or annular-ring coupling cavities. The selection of the type of coupling cavity is not critical to the thermal cooling approach to be described below. In fact, a standing-wave mode of operation is not critical.

Referring now to FIGS. 2, 3 and 4, the abutment surface 54 of the half-cell member 40 is brazed to an entrance plate 80 having an electron beam opening 82 for introduction of charged particles into the first accelerating cavity 72. The beam of charged particles passes through each of the accelerating cavities 72, 74 and 78 and is focused and accelerated. The exit velocity of the output beam is determined by a number of factors, including the number of accelerating cavities within the accelerator device.

The entrance plate 80 and the half-cell members 40, 64, 66, 68 and 70 are interconnected using a brazing process. Wire of brazing material is introduced into grooves and is activated using conventional techniques. An acceptable brazing material is the alloy made of Ag, Pd and Ga. For example, the contents may be 82% Ag, 9% Pd and 9% Ga. In FIGS. 2 and 3, circular grooves 84 and 86 are formed concentrically about the beam-axis opening 50. These openings are filled with the braze material during the interconnection of the monolithic half-cell members. There is also a circular groove 88 for braze material that is concentric with an opening 90 through the upper portion 58 of the monolithic member. This opening 90 is used for attachment of a fastener, not shown.

Referring now to FIGS. 1, 2, 5 and 6, the internal coolant flow path 32 is formed by fabricating each of the monolithic half-cell members 40 to include at least one of the coolant passageways 42–48. The coolant passageway 48 is coaxially aligned with coolant passageways through each of the monolithic half-cell members that form the accelerator device 14. Consequently, when the device-input and device-output conduits 36 and 38 are connected to the coolant passageway 48 in the monolithic member, a flow of liquid coolant can be employed to conduct thermal energy away from the accelerator device.

As previously noted, the concern in providing internal cooling of a clinical linac relates to the number of member-to-member interfaces through which the coolant must pass. This concern is addressed in the illustrated embodiment by providing a braze dam about each of the coolant passageways 42–48 and by providing a leakage-release path for each of the coolant passageways to safely conduct any leakage that does escape.

In FIGS. 5 and 6, the braze dam is formed by inserting a ring of braze material into an inner groove 92. Preferably, the surface against which the first face 52 is to abut includes a corresponding ring of braze material. When the two rings are brazed together, the coolant passageway 48 is sealed. Consequently, if liquid coolant is released at the interface of the two surfaces, the braze dam formed at groove 92 prevents the liquid from reaching any region that would be adversely affected by the introduction of the liquid. Nevertheless, the first face 52 also includes an arcuate groove 94 that provides the leakage-release path, should the braze dam not operate as intended. The leakage-release path has a configuration of a major sector of a circle that is truncated by the edge of the half-cell member 40. Any coolant that reaches the leakage-release path will either remain within the groove 94 or will be forced from the path upon reaching the edge of the half-cell member. Optionally, an absorbent member may be located at the edge of the monolithic member to contain any liquid that passes from the leakage-release path 94.

As shown in FIG. 2, each of the four coolant passageways 42–48 is sealed within a braze dam that is to be formed by a braze ring within groove 92. Moreover, each of the coolant passageways has a separate liquid-release path formed by a circular groove 94 that is truncated at the edge of the half-cell member 40.

The arrangement of a circular groove 92 and an outer truncated groove 94 is duplicated at the abutment region 54 on the second face of the half-cell member. This is shown in FIG. 6. An inner groove 96 is formed to be filled with a ring of braze material to isolate the coolant passageway 48. An outer groove 98 functions as the leakage-release path. The outer groove has the same arcuate shape as the leakage-release path 94 at the first face 52 of the monolithic member. The leakage-release path 98 conducts any escaped coolant away from leaking into the accelerating cavity formed by the monolithic member.

Optionally, the leakage-release paths may take other forms. That is, the paths need not have the arcuate configuration shown in FIGS. 2 and 5. However, the illustrated embodiment does provide advantages with respect to ease of manufacture.

The internal, multi-passageway cooling approach of FIGS. 2–6 more efficiently regulates the temperature of the clinical linac, as compared to the conventional approach of externally cooling the accelerator device. Moreover, since the coolant passages are formed directly into the cavity-defining members, assembling the accelerator device does not require attaching separate coolant conduits.

I claim:

1. In a clinical device for accelerating charged particles along a beam axis for medical purposes, an assembly comprising:

a plurality of monolithic cavity-defining members connected to form a series of accelerating cavities aligned along said beam axis, said cavity-defining members having coolant passageways that are interconnected to form at least one continuous coolant flow path through said plurality of cavity-defining members, wherein adjacent cavity-defining members are in an abutting relationship and said coolant passageways of said adjacent cavity-defining members are aligned for member-to-member transfer of liquid coolant along said coolant flow path;

a leakage-release path at abutting surfaces of said adjacent cavity-defining members, said leakage-release path being a channel in at least one of said abutting surfaces, said channel dividing a surface region proximate to said coolant passageways from a surface region proximate to said beam axis thereby reducing susceptibility of said liquid coolant leaking into one of said accelerating cavities; and braze material separating said coolant flow path from said leakage-release path along said abutting surfaces of said adjacent cavity-defining members.

2. The assembly of claim 1 wherein said leakage-release path extends to edges of said abutting surfaces of said adjacent cavity-defining members.

3. The assembly of claim 1 wherein said leakage-release path has an arcuate configuration, said arcuate configuration being a major sector of a circle that is truncated at edges of said adjacent cavity-defining members.

4. The assembly of claim 1 wherein said coolant passageways of said cavity-defining members are bores extending through said cavity-defining members, said bores being generally parallel to said beam axis.

5. The assembly of claim 4 wherein said cavity-defining members have at least four continuous flow paths arranged symmetrically about said beam axis.

6. A clinical system for delivering charged particles for medical applications comprising:

a source of said charged particles;

a particle accelerator having an input connected to said source to receive said charged particles and having a plurality of particle accelerating cells, said particle accelerator having a beam path extending through each of said cells to an exit window and having an internal flow path for flow of a liquid coolant through said cells, said particle accelerator further having a liquid inlet at a first end and a liquid outlet at a second end, said liquid inlet being connected to said liquid outlet by said internal flow path, said particle accelerator including a plurality, of abutting cavity-defining members that form said cells, each cavity-defining member having a coolant passageway, said internal flow path through said particle accelerator being formed of aligned coolant passageways through said cavity-defining members;

a source of coolant connected to said liquid inlet;

a signal source in energy-transfer engagement with said charged particles within said particle accelerator;

means for applying radiation to a patient in response to an exit beam of accelerated charged particles from said exit window, and brazed areas that surround said internal flow path at each of said abutting cavity-defining members, such that said brazed areas isolate said internal flow path from said particle accelerating cells and said beam path.

7. The system of claim 6 further comprising a leakage-release path at each interface of abutting cavity-defining members each leakage-release path being parallel to a plane that is perpendicular to an axis through said coolant passageways of said abutting cavity-defining members.

8. The system of claim 7 wherein said leakage-release paths separate said internal flow path from said beam path at said interfaces of abutting cavity-defining members.

9. The system of claim 7 wherein said leakage-release paths are surface channels in surfaces of said cavity-defining members.

10. A monolithic member for attachment to other monolithic members in forming a linear accelerator comprising:

a monolithic structure having first and second faces, said second face having a contour that defines at least a portion of an accelerating cavity, said monolithic structure having a beam passageway that extends from said first face to said accelerating cavity for passage of a beam of charged particles and having a coolant passageway that is substantially parallel to said beam passageway for a flow of liquid coolant, said first face having a leakage-release channel that isolates a generally planar first region proximate to said coolant passageway from a generally planar second region that is proximate to said beam passageway, and said second face having a leakage-release channel that isolates a generally planar third region proximate to said coolant passageway from a generally planar fourth region that is proximate to said accelerating cavity.

11. The monolithic member of claim 10 wherein said monolithic structure is a half-cell member having braze areas for attachment to at least one second half-cell member.

12. The member of claim 11 wherein said braze areas include a groove surrounding said coolant passageway within said leakage-release channel.

13. The member of claim 10 wherein said monolithic structure includes a plurality of coolant passageways arranged about said accelerating cavity that is at least partially defined by said contour of said second face.

14. The member of claim 13 wherein said monolithic member includes a separate leakage-release channel for each of said coolant passageways.

\* \* \* \* \*